United States Patent [19]

Petersen et al.

[11] 4,134,925
[45] Jan. 16, 1979

[54] AR-OCTAHALOGENDIPHENYLETHER-4,4-DIMETHANOLS

[75] Inventors: Egon N. Petersen, Neunirchen-Seelscheid; Klaus Schrage, Königswinter-Uthweiler, both of Germany

[73] Assignee: Dynamit Nobel Aktiengesellschaft, Troisdorf, Bezirk Cologne, Germany

[21] Appl. No.: 709,058

[22] Filed: Jul. 27, 1976

[30] Foreign Application Priority Data

Jul. 31, 1975 [DE] Fed. Rep. of Germany ....... 2534209

[51] Int. Cl.$^2$ .............................................. C07C 43/20
[52] U.S. Cl. .................................... 568/637; 560/138; 568/639; 568/638
[58] Field of Search ..................................... 260/613 R

[56] References Cited

U.S. PATENT DOCUMENTS

| 3,100,796 | 8/1963 | Trapp et al. | 260/613 R X |
|---|---|---|---|
| 3,170,959 | 2/1965 | Trapp | 260/613 R |
| 3,269,973 | 8/1966 | Doedens et al. | 260/613 R X |
| 4,014,940 | 3/1977 | Ume et al. | 260/613 R X |

Primary Examiner—Bernard Helfin
Attorney, Agent, or Firm—Sprung, Felfe, Horn, Lynch & Kramer

[57] ABSTRACT

Compounds of the formula:

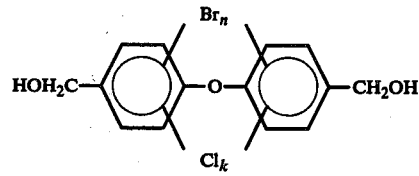

The compounds can be produced by reacting the corresponding 4,4'-bis-(halogenmethyl)-ar-octahalogendiphenylethers with at least 2 moles of alkali acetate or formiate in the presence of alcohol as transesterification agent and solvent. The compounds are useful as intermediates for the production of insecticides, herbicides or hydrophobizing agents.

6 Claims, No Drawings

AR-OCTAHALOGENDIPHENYLETHER-4,4-DIMETHANOLS

The present invention relates to aroctahalogendiphenylether-4,4'-dimethanols of the general formula

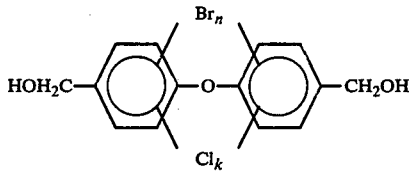

which have not previously been described and in which the index n represents positive numbers from 0 to 8 and the index k represents 8 - n.

The dimethanol groups are in the para position with respect to the other oxygen.

Of the new substances the octachloro compounds, on the one hand, are of special value, and on the other hand the bromine-rich compounds beginning with $Br_6Cl_2$, and particularly the substitution compounds from $Br_7Cl_1$ to $Br_8$ are of special value.

The preparation of the new compounds can be accomplished in various ways, such as saponification, for example, but it is accomplished very expediently and with a high yield by the reaction of the halogen methyl compound corresponding to the particular glycol involved, with alkali acetates followed by transesterification of the diacetates with alcohols.

In this case, alkali acetates, or also alkali formiates, especially of sodium or potassium, are used in amounts of at least 2 moles per mole of halogen methyl compound, usually an excess of up to about 25%, in the presence of alcohols as transesterification agents and solvents in amounts of 10 to 300 times the stoichiometric.

Methanol and alkyl ethers of glycols are preferred, especially ethylene glycol monomethyl ether, although primary alcohols of 2 to 4 carbon atoms and their ethers can also be used.

Temperatures ranging from 80 to 180° C, and preferably from 100 to 140° C, are desirable. The pressure can be atmospheric pressure, self-pressure in a closed vessel, or a slight excess pressure.

Alcohol and the alkyl acetate or formiate that forms are removed by distillation during the reaction, the addition of alkali alcoholates, especially sodium methylate, dissolved in the correponding alcohol, being desirable for the acceleration of the transesterification.

The reaction takes place as follows:

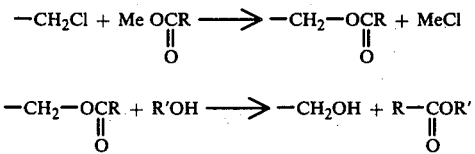

wherein R represents $CH_3$ or H and R' represents the above-named alkyl radicals and Me is an alkali metal ion.

It is to be understood that, in the formation of the dimethanols, the halogen in the nucleus is not attacked and remains unaltered, as is not the case in the preceding chlorination of the side chain in which, depending on the reaction conditions, small portions of bromine are displaced from the nucleus by chlorine and enter partially into the side chain.

The glycols of the General Formula I are valuable intermediates for the production of insecticides, herbicides or hydrophobizing agents.

Bis-(halogen methyl) compounds are used as the starting materials for the production of the new glycols of the invention, the term "halogen" referring to chlorine or bromine, with substitution in the nucleus that is of the same kind and amount as in the dimethanol compound that is to be prepared--preferably, and to special economic advantage, chloromethyl compounds such as those which are easily obtainable by a process for the preparation of ditolyl ethers chlorinated in the side chain and halogenated in the nucleus which is described in the copending German patent application P 25 34 210.3, filed July 31, 1975, U.S. Ser. No. 709,057, filed July 27, 1976.

The following, for example, can serve as starting substances: 4,4'-bis-(chloromethyl)-ar-octabromodiphenyl ether, 4,4'-bis-(chloromethyl)-ar-octachlorodiphenyl ether, 4,4'-bis-(chloromethyl)-ar-monochloroheptabromodiphenyl ether, or mixtures of 4,4'-bis-(chloromethyl)-ar-octahalogendiphenyl ethers of different degrees of bromination or chlorination, as well as the corresponding bis-(bromomethyl) compounds, or mixtures formed in the chlorination of the side chain by halogen exchange with nuclear bromine, of bis-(halogen methyl) compounds with a highly predominant amount of chloromethyl groups and a lesser amount of bromomethyl groups.

The substances referred to herein as ar-octahalogendiphenylether-4,4'-dimethanols can also be referred to as 4,4'-bis-(hydroxymethyl)-ar-octahalogendiphenylethers without change of meaning.

The reaction is performed in the presence of solvent. The function of the solvent is to form a partly or fully homogeneous reaction mixture. Suitable solvents are alkylene glycol monoalkyl ethers as ethylene glycol monomethylether and corresponding ethyl, propyl, butyl etc. ethers, and the propylene-1, 2 and -1,3 glycol and butylene-1,4 and 2,3 glycol alkyl ethers or dioxane, dimethyl formamide dimethylsulfoxide, sulfolane, etc. The new ar-octahalogenodiphenylether-4,4'-dimethanols are useful in the production of the (meth)acrylates by esterification with (meth)acrylic acid. ar-octabromodiphenylether-4,4'-dimethanol-bisacrylate according the equation below is formed:

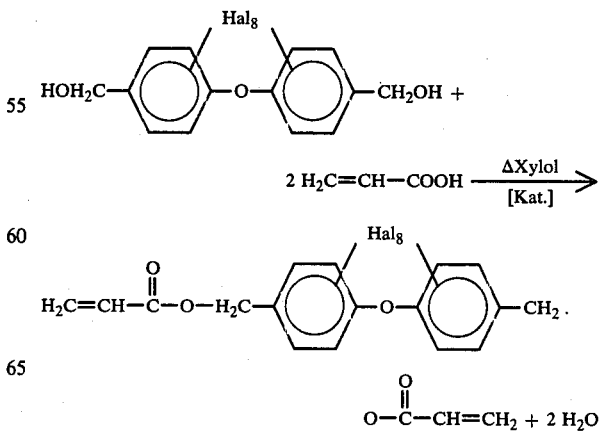

In a two-liter round flask equipped with stirrer and water condenser, 431 g (0.5 mole) octa produced according example 1, 3 liters of xylene and 80 g (~1,1 mole) were heated to the poiling temperature in presence of 2 g hydroquinone monomethyl ether as polymerization inhibitor and 5 g p-toluenesulfonic acid as esterification catalyst. When the theoretical amount of 18 g(=1,0 mole) water was found in the water condenser and no more water was formed the reaction is complete. The reaction time is 11 to 14 hours. The reaction mixture is inhomogeneous during the reaction. After cooling to room temperature the reaction mixture was separated by suction filtering, washed with xylene and dried. 447 g raw bis-acrylate of given formula was obtained mp. 161–165° C, yield 92 % of the theoretical amount.
bromodiphenylether-4,4'-dimethanol Recristalliced the mp. was 172 to 174. Elemental Analysis: Calc.: C 24,7 % ; Br 65,9 %. Found: C 24,58 % ; Br 65,7 %. The corresponding bis-methacrylate was prepared from 1,1 mole methacrylic acid instead of the acrylic acid. The melting point is mp. 176 – 179° C, the yield is 88 %. In quite corresponding manner the octachlorodiphenylether-4,4'-dimethanolbisacrylat was produced from product of example 3, having a melting point of 137–140° C and the corresponding octachlorodiphenylether-4,4'-dimethanolbismethacrylate was produced in a yield of 84 % and of the melting point of 103–107° C after recrystallization from ethyleneglycole monomethylether. All further dimethanols with as well bromine and chlorine substituents form bis(meth)acrylates in the same manner. The so produced bis-acrylates and bis-methacrylate are very valuable flame retardents for e.g. polyethylene or polyesters like polyethylene tere=and isophthalates in amounts of 2 to 15 wt.-%. No sweeping out of these flame retardents is observed and the flame extinguishing properties are very good as self extinction is obtain by low amounts of the bis(meth) acrylates of 8 to 12 wt-% of the plastic products. Furthermore these bis-(meth acrylates are very useful as monomers or comonomers in the production of flame retardent polymers and copolymers, partly beeing reticulated and not meltable as to the two unsaturated (meth)-acrylate groups per molecule. So plastics with contents of eg. 2–20 wt.-% of the (co)polymers have a very good termal stability during the forming of the plastics products. Very valuable is the fact that no decomposition of the flame retardent (co)polymer occurs at temperatures below 280° C. The so produced ar-octabromodiphenylether-4,4'-dimethanol-bis-acrylate in an amount of 130° C is soluted in 150 ml methylglycole and 3 g dicumylperoxide is added as polymerization catalyst. After heating to 140° C for 5 hours the polymer is fallen out and is sucked off, washed with water and dried at 160° C. The polymer is unsoluble and unmeltable the bromine content beeing 65 wt-% and the chlorine content 1,2 wt-%. 12 g is this polymer, 5 g of $Sb_2O_3$ and 83 g of polyethylene of high density were worked together in a two screw extruder and from the resulting granulate plates of 4 mm are pressed. By means of a bunsen burner the plates are inscended are self-extinguishing within 5 seconds. In the same manner as described above the named brominated and chlorinates methacrylated were polymerised. Added to polyethylene the flame resulting properties were as noted above.

EXAMPLES

The following examples are intended for the purpose of explaining the invention, without limiting it.

EXAMPLE 1 ar-Octabromodiphenylether-4,4'-dimethanol (a) Preparation of the dichloromethyl starting compound

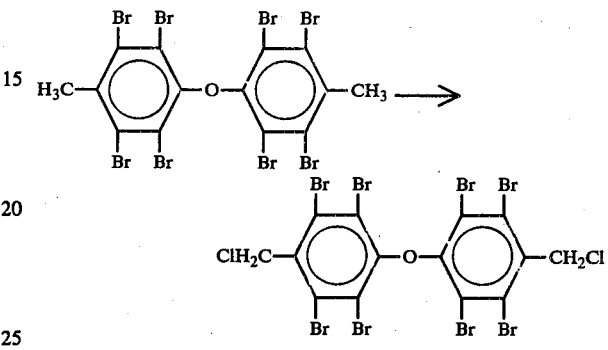

In a two-liter round flask equipped with condenser, stirrer, thermometer and gas feed tube, 630 ml of hexachlorobutadiene, 415 g (0.5 mole) of octabromo-p-p'-ditolyl ether (M.P. 258–261° C; iron content 40 ppm) and 0.45 g of ethylenediamine tetraacetic acid were heated, with stirring, at 175° C. Most of the starting substance was thereby dissolved, and the introduction of chlorine onto the surface of the slowly stirred mixture was begun. The chlorination of the side chains immediately begain with a strong production of hydrogen chloride. The introduction of chlorine was continued at a temperature of about 180° C, until bromine vapors were clearly seen in the flask, which was the case within about 2½ hours, and then the chlorine input was terminated.

A part of the 4,4'-bis-(chloromethyl)-ar-octabromodiphenyl ether that had formed precipitated while the chlorination was in progress. The batch was cooled to room temperature, the brownish crystallizate was suction filtered, washed with petroleum ether and dried. 408 grams (91%) of dichloromethyl compound with a melting point of 270–284°. C were obtained.

Upon recrystallization from xylene (10 g from 80 ml), a colorless crystallizate was obtained having a melting point of 283–288° C.

Elemental Analysis: $C_{14}H_4Br_8Cl_2O$ (898.36): Calculated: C 18.72%; H 0.45%; Br 71.16%; Cl 7.89%; O 1.78%: Found: C19.09%; H 0.39%; Br 71.3%; Cl 7.6%; O 1.68%.

A repetition of the experiment, in which 2.075 kg (2.5 moles) of octabromo-p,p'-ditolyl ether, 3.1 liters of hexachlorobutadiene and 2.1 g of ethylenediaminetetraacetic acid were used, produced, after about 4 hours of chlorination at 185° C, a dichloromethyl compound in a 92% yield, having a melting point of 281–284° C without recrystallization.

(b) Preparation of the glycol

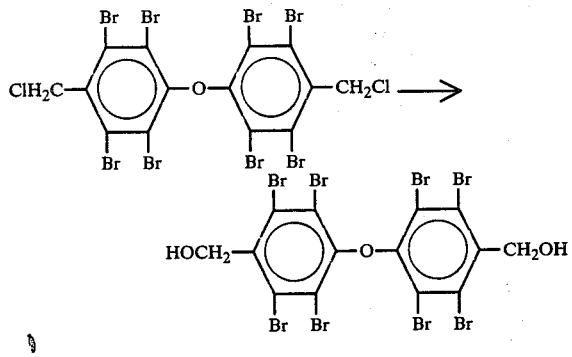

In a ten-liter four-necked flask equipped with stirrer, thermometer, dropping funnel and column with column head, 4 liters of ethylene glycol monomethyl ether (methyl glycol) of low water content and a boiling point of 122–126° C were placed, in which 1.797 kg (2 moles) bis-(chloromethyl) compound prepared as in part a) was suspended cold together with 362 g (4.4 moles) of anhydrous sodium acetate. Then the mixture was heated, with stirring, to ebullition, whereupon the reaction began at about 115° C with slight foaming and the formation of sodium chloride.

The reaction mixture was boiled for another 2 hours in the column, while aqueous methyl glycol of 108–125° C slowly distilled out in the vapor. The internal temperature in the meantime increased to 127° C. 400 ml of liquid was distilled out. Then the reaction mixture was cooled down 65° C and 2 liters of methanol were added through the dropping funnel; then 70 ml of 3N NaOCH$_3$ solution (in methanol) was added, plus 5 g of solid sodium methylate as transesterfication catalyst. The alkalinity of the reaction mixture then amounted to about pH 9.

The mixture was again heated at ebullition (76–77° C internal temperature, and an azeotropic mixture of methanol and methyl acetate was distilled out as it formed. The head temperature amounted initially to 55° C, increasing toward the end to 64–65° C. After 9 hours of distillation, 10 ml of 3N sodium methylated solution was added and the distillation was continued until the distillate had the index of refraction of pure methanol.

Over a distillation period of about 16 hours, one liter of liquid was distilled out. The glycol that had formed precipitated in microcrystalline form while the distillation was in progress.

The batch was cooled to room temperature, the solids were suction filtered and washed, first with a little methanol and then with water until all of the sodium chloride had been removed, and finally the virtually colorless raw glycol was dried.

The yield was 1.48 kg, corresponding to 86% of the theoretically possible quantity. Crude melting point: 284–290° C.

Concentration of the filtrate yielded an additional 53 g (3%) having a melting point of 292–297° C. 100 g of raw glycol, recrystallized from 1.2 liters of hexachlorobutadiene, yielded colorless crystals of a melting point of 292–298° C.

Elemental anaylsis: $C_{14}H_6Br_8O_3$ (861.47): Calculated: C 19.52% H 0.70% Br 74.20% Cl 0.00% O 5.58%: Found: C 20.31% H 0.71% Br 70.61% Cl 3.00% O 5.49%. This corresponds to the following gross composition: $C_{14}H_6Br_{7.3}Cl_{0.7}O_3$ (830.34).

EXAMPLE 2

Preparation of an ar-octahalogendiphenylether-4,4'-dimethanol from an ar-octahalogen-p,p'-ditolylether obtained by the bromochlorination of p,p'-ditolylether:

(a) Bromochlorination of p,p'-ditolylether

In five procedures using the mother liquor of each previous procedure, a total of 773 g (3.9 moles) of ditolylether was reacted with 3.962 kg (34.3 moles) of bromine chloride.

Yield: 2.968 kg, M.P. 258–262° C, composition $C_{14}H_6Br_{7.5}Cl_{0.5}$ (807): Calculated: C 20.8% H 0.8% Br 74.2% Cl 2.2% O 2.0%: Found: C 21.3% H 1.0% Br 74.0% Cl 2.2% O 1.8%.

This corresponds to a utilization of 94% of the p,p'-ditolylether and of 80% of the bromine (the 231 g of product in the mother liquor of the last procedure of the series was not worked up).

A typical batch is described herewith: In a four-necked flask equipped with stirrer, reflux condenser, a cooled dropping funnel and a thermometer, 198 g (1 mole of p,p'-ditolylether was dissolved in 900 ml of 1,2-dichloroethane, and 16.2 g (0.1 mole) of anhydrous iron(III) chloride was added. With external cooling, at 15° C, 1.016 kg (8.8 moles) of bromine chloride was added drop by drop, which had previously been prepared in the refrigerated dropping funnel by the introduction of chlorine into bromine. The addition of the bromine chloride was completed in 3 hours. Then the mixture was slowly heated to ebullition and boiled with refluxing for another 2 to 3 hours.

After cooling, the product was suction filtered, stirred up in 250 ml of 1,2-dichloroethane, and then suction filtered again. The mother liquor was combined with the washing dichloroethane, concentrated to 900 ml, and, after the addition of 12.2 g (0.075 mole) of anhydrous iron(III) chloride, it was used for the next batch.

(b) Side chain chlorination

In the apparatus described in Example 1 a), 2.45 kg (approx. 3 moles) of bromochlorination product which had been prepared in accordance with Example 2 a), and had the composition described in 2 a) and an iron content of 109 ppm, was suspended in 3.1 liters of hexachlorobutadiene; 2.5 g of ethylenediaminetetraacetic acid was added and chlorination was performed under the conditions described in Example 1 a). The chlorination time was 6½ hours.

The bis-(chloromethyl) derivative precipitated while the chlorination was in progress. After the reaction mixture had cooled to room temperature, the product was suction filtered, washed with a little hexachlorobutadiene, then rewashed with petroleum ether, and dried. 2.41 kg (92%) of a pale brownish crystallizate of M.P. 274–84° C was obtained. Colorless crystals were obtained by recrystallization from xylene (10 g from 70 ml), and melted at 278–285° C. They had the following composition:

$C_{14}H_4Br_{7.6}Cl_{2.4}O$ (880.58): Calculated: C 19.09% H 0.45% Br $_{68.9}$ % Cl 9.66% O 1.82%: Found: C 19.31% H 0.41% Br 68.70% Cl 9.54% O 2.01%.

(c) Preparation of the glycol

In the apparatus described in Example 1 b), 3.5 liters of methyl glycol (B.P. 122–126° C) were placed, and 1.348 kg (1.5 moles) of raw bis-(chloromethyl) compound from Example 2 b) plus 271 g (3.3 moles) of anhydrous sodium acetate are suspended cold therein.

The mixture was then heated to ebullition, with stirring, the reaction starting up at about 100° C. Boiling continued for 2 hours on the column, while a mixture of water and methyl glycol was slowly distilled off, the temperature in the reaction mixture rising to 127° C. 300 ml of distillate was withdrawn.

After the mixture had cooled to 65° C, 1.5 liters of methanol, 70 ml of 3N sodium methylate solution and 5 g of solid sodium methylate were added, and the mixture was heated again to ebullition. The procedure continued as described in Example 1 b), 680 ml of distillate being withdrawn in 12 hours.

Most of the glycol precipitated while the reaction was in progress. The solids were suction filtered from the cooled reaction mixture, washed free of chloride, and the raw glycol was vacuum dried at 100° C. The yield was 1.182 kg (91.5%), with a melting point of 285–292° C. 5 g of the product was recrystallized from hexachlorobutadiene and yielded colorless crystals melting at 291–298° C.

Elemental analysis: $C_{14}H_6Br_{7.1}Cl_{0.9}O_3$ (821.49): Calculated: C 20.47% H 0.74% Br 69.06% Cl 3.88% O 5.84%: Found: C 20.41% H 0.66% Br 69.32% Cl 4.01% O 5.66%.

EXAMPLE 3

Preparation of ar-octachlorodiphenylether-4,4'-dimethanol

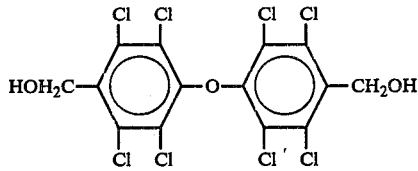

p,p'-ditolylether (3 moles) was chlorinated in the nucleus in hexachlorobutadiene (2 liters) in the presence of anhydrous iron(III) chloride (30 g) at 150–160° C to form ar-octachloro-p,p'-ditolylether. Yield 84%.

The ar-octachloro-p,p'-ditolylether thus obtained was then chlorinated on the side chains as in Examples 1 a) and 2 b), using 1.75 moles in 1.1 liters of hexachlorobutadiene. Chlorination temperature 170° C. The yield of 4,4'-bis-(chloromethyl)-ar-octachlorodiphenylether was 819 g (87%), M.P. 211–216° C. 15 g thereof was twice recrystallized from 45 ml of hexachlorobutadiene, and then yielded colorless crystals of a melting point of 224–227° C, with a saponification number of 201 mg of KOH per gram of substance (calculated: 207).

Elemental analysis: $C_{14}H_4Cl_{10}O$ (542.71): Calculated: C 30.98%, H 0.75%, Cl 65.32%, O 2.95%: Found: C 30.74%, H 0.69%, Cl 65.45%, O 3.04%.

For the preparation of ar-octachlorodiphenylether-4,4'-dimethanol, the following were combined in the apparatus of Example 1 b):

2 liters of methylglycol (B.P. 122–126° C)

679 g (1.25 moles) of raw bis-(chloromethyl) compound and 247 g (3 moles) of anhydrous sodium acetate.

The reaction with the sodium acetate started up at about 90° C. In two hours, 310 ml of liquid had been distilled out at the column, and then, after cooling to 65° C, 1 liter of methanol, 70 ml of 3N sodium methylate solution, and 5 g of solid methylate were added. The transesterification was performed as described in the preceding examples. The transesterification time was 15 hours and 475 ml of liquid was distilled out.

The reaction mixture, from which a portion of the glycol plus sodium chloride had already precipitated, was brought to room temperature, and then the raw glycol was suction filtered, washed free of salt with water, and dried.

The yield was 492 grams, corresponding to 78% of the theoretically possible quantity. The substance was a colorless, microcrystalline powder whose melting point was 261–268° C. 10 grams thereof were recrystallized from 60 ml of methyl glycol and yielded well-defined crystals of a melting point of 266–269° C.

Elemental Analysis: $C_{14}H_6Cl_8O_3$ (505.82): Calculated: C 33.24%, H 1.19%, Cl 56.07%, O 9.49%: Found: C 33.35%, H 1.11%, Cl 56.13%, O 9.38%.

What is claimed is:

1. ar-Octahalogendiphenylether-4,4'-dimethanol of the formula:

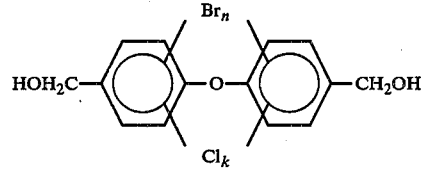

wherein the n represents a number of from 0 to 8 and the k represents 8 - n.

2. Compound of claim 1, which is ar-Octabromodiphenylether-4,4'-dimethanol.

3. Compound of claim 1, having the gross formula elemental analysis: $C_{14}H_6Br_{7.1}Cl_{0.9}O_3$.

4. Compound of claim 1, which is ar-octachlorodiphenylether-4,4'-dimethanol.

5. Compound of claim 1, wherein n is at least 6.

6. Compound of claim 1, wherein n is at least 7.

* * * * *

UNITED STATES PATENT AND TRADEMARK OFFICE
CERTIFICATE OF CORRECTION

PATENT NO. : 4,134,925
DATED : January 16, 1979
INVENTOR(S) : Egon Norbert Petersen and Klaus Schrage It is certified that error appears in the above-identified patent and that said Letters Patent are hereby corrected as shown below:

The title, change "-4,4-" to --  -4,4'-  --;

Col. 1, line 20, change "other" to --ether--;

Col. 3, line 2, change "octa" to --octabromodiphenylether-4,4'-dimethanol --;

Col. 3, line 17, cancel "bromodiphenylether-4,4'-dimethanol" ;

Col. 3, line 18, change "Recristalliced" to --recrystallized--;

Col. 3, line 30, change "recristallization" to --recrystallization--;

Col. 3, line 47, change "termal" to --thermal--;

Col. 4, line 36, change "begain" to --began--;

Col. 6, line 62, change "$Br_{68.9}\%$" to -- Br 68,97%--.

Signed and Sealed this

Third Day of July 1979

[SEAL]

Attest:

LUTRELLE F. PARKER

*Attesting Officer*  *Acting Commissioner of Patents and Trademarks*